United States Patent [19]

Jurkowski et al.

[11] Patent Number: 5,667,301
[45] Date of Patent: Sep. 16, 1997

[54] DEVICE FOR MEASURING THE HEAT CONDUCTIVITY OR HEAT CAPACITY OF AN INJECTABLE OR NON-INJECTABLE MATERIAL

[75] Inventors: Thomasz Jurkowski, Nantes; Yvon Jarny, Orvault; Didier Delaunay, Nantes, all of France

[73] Assignee: Universite de Nantes, Laboratoire de Thermocinetique de l'Isitem, Nantes Cedex, France

[21] Appl. No.: 397,089

[22] PCT Filed: Sep. 10, 1993

[86] PCT No.: PCT/FR93/00868

§ 371 Date: Mar. 7, 1995

§ 102(e) Date: Mar. 7, 1995

[87] PCT Pub. No.: WO94/05999

PCT Pub. Date: Mar. 17, 1994

[30] Foreign Application Priority Data

Sep. 10, 1992 [FR] France .................... 92 10805

[51] Int. Cl.[6] .................... G01N 25/20; G01N 25/18
[52] U.S. Cl. .................... 374/43; 374/44
[58] Field of Search .................... 374/43, 44, 29

[56] References Cited

U.S. PATENT DOCUMENTS

| | | | |
|---|---|---|---|
| 3,045,473 | 7/1962 | Hager, Jr. | 374/44 |
| 3,075,377 | 1/1963 | Lang | 374/44 |
| 4,259,859 | 4/1981 | Iida et al. | 374/43 |
| 4,630,938 | 12/1986 | Piorkowska-Dalczewska et al. | 374/44 |
| 5,005,985 | 4/1991 | Piorkowska-Galeska et al. | 374/43 |

FOREIGN PATENT DOCUMENTS

| | | | |
|---|---|---|---|
| 0 124 104 | 11/1984 | European Pat. Off. | |
| 0855463 | 8/1981 | U.S.S.R. | 374/43 |
| 1133525 | 1/1985 | U.S.S.R. | 374/44 |
| 1545148 | 2/1990 | U.S.S.R. | 374/44 |

OTHER PUBLICATIONS

E. Piorkowska et al., "Measurements of thermal conductivity of materials using a transient technique. II. Description of the apparatus", *Journal of Applied Physics*, vol. 60, No. 2, Jul. 1986, New York, pp. 493–498.

A. Degiovanni et al., "Une nouvelle technique d'identification de la diffusivite thermique pour la methode 'flash'", *Revue de Physique Appliquee*, vol. 21, No. 3, Mar. 1986, Paris, pp. 229–237.

H. Lobo et al., "Measurement of Thermal Conductivity of Polymer Melts by the Line–Source Method", *Polymer Engineering and Science*, vol. 30, No. 2, Jan. 1990, pp. 65–70.

A. Degiovanni, "Diffusivite et methode flash", *Revue Generale de Thermique*, vol. XVI, No. 185, May 1977, pp. 420–442.

*Primary Examiner*—Diego F. F. Gutierrez
*Attorney, Agent, or Firm*—Young & Thompson

[57] ABSTRACT

The measuring device comprises two flat-wall heat exchangers (3a, 3b), one to each side of a flat plate (1), two samples (2a, 2b) of similar thickness (E) of the material being tested, placed between the outer surface of the heat exchanger (3a, 3b) and one surface of the central plate (1), a device for positioning and holding the heat exchangers (3a, 3b) and at least two temperature sensors, one of which (T2) consisting of a thermocouple is incorporated in the central plate (1), the other (T1) also consisting of a thermocouple, being incorporated in the outer wall of the plate of one of the heat exchangers (3a). Application in the injection of plastics.

7 Claims, 5 Drawing Sheets

DEVICE FOR MEASURING THE HEAT CONDUCTIVITY OR HEAT CAPACITY OF AN INJECTABLE OR NON-INJECTABLE MATERIAL

FIELD OF THE INVENTION

The present invention relates to a measuring device to measure continuously parameters such as heat conductivity or heat capacity of an injectable or non-injectable material and if desired to establish the kinetic laws of said material.

BACKGROUND OF THE INVENTION

Methods consisting in determining the thermal properties (heat conductivity or heat capacity) of various materials are numerous. There are thus known so-called continuous measurement methods which have the drawback of being long to use while permitting only each time the measurement of a single value. These methods such as those which utilize a heat shielded plate or a radial flux do not permit visualizing the changes in a material such as the change of structure in the course of measurement.

Another large group of measurement methods relates to methods for measuring a transitory regime. A first so-called flash method described particularly in the article of A. Degiovanni: "Diffusivity and Flash Method", Revue Generale de Thermique, Volume XVI, N° 185 of May, 1977, has the drawback of providing only a mean value for a given interval of variation of the temperature of the material. A second method using a shock probe described in the article A. Lobo/C. Cohen "Measurement of thermal conductivity of polymer melts by line-source methods", Polymer Engineering and Science—January, 1990, Volume 30, N° 2, and a study of the thermal transfer coupling and preliminary physico-chemical transformation ratio, 1987, B. Garnier/D. Delaunay, has fairly poor precision (in the range 10–20%). This method is moreover fairly long to use when it is desired to make a measurement of elevated temperatures because it is necessary before the measurement to bring the conductivity meter and the materials to a uniform temperature. As a result, the methods described above are usable only with difficulty if the transformations take place in the material during the duration either of preparation or of performance of the measurement. They are therefore of little applicability in this case. Such is the case in particular with the process and device described in EP-A-0.124.104. In this patent, there is proposed a device which is generally similar in physical arrangement to the device of the invention to determine the thermal conductivity and thermal capacity of materials. The essential difference from the present invention resides in the use of a heating element disposed between two specimens which requires modifying linearly the temperature and in making the supposition that over a given range of temperature the conductivity is constant. Because of this, again, by means of such a device, account is not taken of the possible transformations of the material.

A third group of methods utilizing algorithms for identification by a reverse method permits avoiding the drawbacks mentioned above (duration of handling, impossibility of making more than one measurement, impossibility of giving results in certain regions of materials in which transformations of the material take place). Their precision however is insufficient. Thus, in certain configurations of measurement of the flows, it is necessary to know precisely the value of certain thermal contact resistances or the thermal conductivity of certain constituent materials of the conductivity meter. These supplemental measurements are not always easy to perform. Moreover, these methods often require the implantation of sensors within the specimens, thus giving rise to a certain number of problems.

SUMMARY OF THE INVENTION

The object of the present invention is therefore to provide a device for measuring parameters such as the conductivity under transitory circumstances which permits said measurement by means of a manipulation and of rapid operation during less than an hour, supplying results in temperature ranges in which transformations of the material take place and having account of the contact resistances at the interfaces of the specimen/constituent elements of the conductivity meter, so as to avoid the necessity for sensors within the specimen.

Another object of the present invention is to provide a device for polyvalent measurement adapted to identify parameters such as the conductivity or capacity of thermoplastic materials or composites having regard for actual conditions of industrial production of said materials.

To this end, the invention relates to a measurement device to measure transitorily parameters such as heat conductivity, heat capacity of a material which is injectable or not, so as to establish the kinetic laws, characterized in that it comprises two heat exchangers with flat walls disposed on opposite sides of a flat plate with parallel walls sufficiently conductive of heat to be considered isothermal and delimiting with said plate two substantially identical chambers, two specimens of the material to be characterized of similar thickness (E), disposed in said respective chambers between the external surface of the exchanger and a surface of the central separation plate so as to be traversed by the heat flow, a device for positioning and for holding the exchangers substantially parallel to the central plate so as to ensure a homogeneous contact pressure between the exchanger walls/external surface of the specimens/surfaces of the central plate, insulation means closing the remaining free edges of said chambers for unidirectional heat flow, and at least two temperature sensors of which one T2 constituted by a thermal couple is integrated into the central plate and of which the other T1 constituted equally by a thermocouple is integrated into the external wall of the plate of one of the exchangers.

According to one preferred embodiment of the invention, the measurement device comprises a third temperature sensor constituted by a thermocouple T3 integrated into the external wall of the second exchanger wall.

The invention also relates to a process for the identification of parameters such as conductivity of the material, characterized in that with the measurement device there is established the curve $T_2$ (t) called object response, in that a model is made of the type of end differences permitting obtaining a model response $\theta$ (t), in that a spacing criterion $J = \Sigma_{k=1}^{n} (\theta_k - T_k)^2$ is defined $\theta_k$: temperature calculated at the instant k.

$T_k$: temperature measured at the instant k.

which permits minimizing the distance between the temperatures measured in the central plate and the temperatures calculated for the same point and at the same instant for the model, said minimization having an iterative character so as to adjust successively the assembly of the parameters according to a method of descent, in that the comparison is stopped when the value of the spacing criterion responds to a stop condition, said stop condition taking place when $J = \Sigma$, $\Sigma$ being considered as negligible.

BRIEF DESCRIPTION OF THE DRAWINGS

Other characteristics and advantages of the invention will become apparent from the reading of the description which follows and the accompanying drawings, said description and drawings are given only by way of examples. In these drawings.

DETAILED DESCRIPTION OF THE DRAWINGS

The measurement device of the invention is adapted to characterize and measure the conductivity and/or the capacity of specimens of materials, whether said materials are ready at the beginning at the measurement or are injected, said materials being adapted to be composite materials, polymers, thermoplastics, materials of low conductivity whose conductivity will be for example less than 2, etc.

Figure 1:
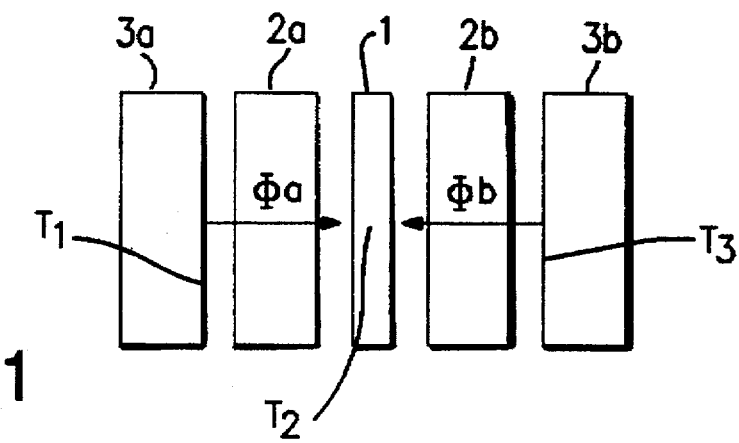
FIG. 1 is a simplified exploded schematic view of a conductivity meter according to the invention.

The constituent elements of the measurement device in particular in this case of a conductivity meter comprise, as shown in FIG. 1, two symmetrical exchangers 3a, 3b with a flat wall permitting reheating or cooling an element in contact therewith and a central separation plate 1 disposed between said exchangers 3a and 3b so as to provide with these latter two identical chambers. These chambers are delimited on the one hand, laterally by the external surfaces of the exchangers 3a and 3b described above and by the single separation plate 1, on the other hand by an insulation which will be defined hereafter and which closes the remaining free edges of said chambers. Within these chambers are disposed the specimens of the materials to be characterized either at the beginning of handling or in the course of handling in the case in which an injectable material is involved.

Figure 8:
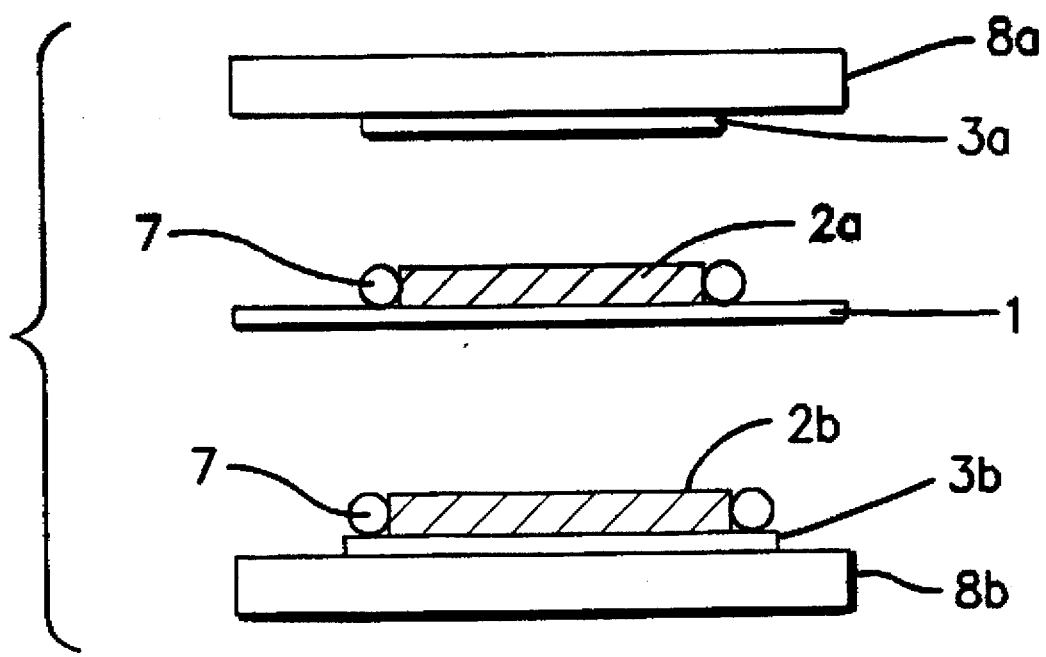
FIG. 8 is a simplified schematic view of a press incorporating the measurement device.

Associated with these two heat exchangers 3a and 3b and with this central separation plate 1, a spacing and gripping device (not shown) permits positioning and holding the exchangers in pressure contact against the specimens themselves in pressure contact against the central separation plate. In the case of an injectable material, this device permits holding the exchangers at a known distance from the separation plate such that the chambers will be of known volume and may be filled for example by injection at any time by a specimen of material to be characterized. In the case of composite materials, for example, it is possible to fix respectively the exchangers 3a and 3b on the facing surfaces of the movable plates 8a, 8b of a press, then to position the specimens of composite material 2a, 2b respectively on the central plate 1 and on the exchanger 3b as shown in FIG. 8. These composites in the form of strata impregnated with resin are held by means of an insulator 7. When the plates of the press are brought together toward the central plate 1 maintained fixed, these plates again compress the external surface of the specimen exchanger so as to ensure homogeneous pressure contact between the exchanger walls/external surfaces of the specimens/surfaces of the central plate. Obviously, thanks to detectors, the distance between the plates of the press and the central plate 1 is known and predetermined so as to permit analysis of parameters identical to that performed in the case in which the measurement is not integrated into a press. Similarly, the case of injectable thermoplastic materials, it is possible to provide injection nozzles opening into each chamber generally in a radial plane at the level of the insulation 7 shown in FIG. 8. Thanks to such arrangements, the characteristics of industrial production are reproduced and the behavior of a large number of materials can be tested.

To obtain unidirectional flow through the two specimens of the material to be characterized, it is necessary to insulate the assembly of the device by completely closing the volume delimited by the respective walls of the exchanger and of the central plate 1. This insulation is obtained by means of an insulator whose conductivity must be low, preferably lower than 0.1 w/m/k and whose heat capacity must also be very low, preferably less than $2\times10^5$ J/kg/k.

The measurement of the temperatures permitting the calculation in particular of the conductivity takes place by means of thermocouples integrated in the central plate 1 and on the walls of the heat exchange plates 3a and/or 3b. Thanks to this particular implantation of the temperature sensors, it is not necessary to implant internal sensors in the specimen of material to be studied, which permits rapid and efficacious handling without damage to the specimen. Among these temperature sensors, there can be a first sensor constituted by a thermocouple T2 integrated into the central separation plate 1, and implanted preferably adjacent the center of symmetry of the conductivity meter constituted by the central plate and the plate heat exchangers. The two other thermocouples T1 and T3 permitting also temperature measurements are integrated on the wall of the exchanger plates. Preferably they are integrated in the immediate vicinity of the external surface of said plates nearer the center of each of the walls. This integration is generally effected by means of fine grooves provided in the surface of said plates and in which the thermocouples are disposed. Thanks to the fact that the single separation plate 1 is subjected to two substantially identical heat fluxes from the two heat exchangers, said flux is Φa, Φb being of opposite direction, it can be considered that the central separation plate 1 is isothermal when the thermal equilibrium of the assembly of the device has been achieved. Because of this hypothesis bearing on the central separation plate 1, it is preferred to use a central separation plate 1 with parallel machined faces such that the variation of the constant thickness will not be more than 0.2%. To confirm the hypothesis consisting in supposing that the temperature remains uniform during all the duration of measurement, it is convenient, on the one hand, that the central plate be of a sufficiently good heat conductive material, on the other hand that the thickness Ep of the central plate 1 will be selected relative to the thickness E of the specimen such that the inequalities (A) and (B) will be maintained as follows:

(A) $(Ep/E)^2 < 0.1\ \alpha_P/\alpha_{E_X} 1/\Delta T$ and (B) $Ep/E \leq 0.5$, in which $\alpha_P$ and $\alpha_E$ are the respective diffusivities of the plate and the specimens and T is the externally imposed temperature region.

The specimen need not have any special dimensions. Thus, to obtain good measurement precision, it is necessary that the ratio (thickness/radius or length of the specimen) be smaller than one third. It is evident however that the specimen could have any shape, circular, rectangular, etc. provided that the insulation perfectly mates with the periphery of said specimen. The thickness of the specimen of the material to be studied should moreover respect the following inequality:

$$E^2 \leq \lambda \times T \times \pi^2 / \gamma \, Cp,$$

in which $\lambda$, $\gamma$, $Cp$ respectively the conductivity, the volumetric mass and the volumetric specific heat at the temperature in question of the specimen of the material to be studied. T constitutes the delay necessary to reach thermal equilibrium of the assembly of the device, this thermal equilibrium being necessary to consider the plate as a heat accumulator of which at any given moment the temperature is uniform. As a result, to permit rapid measurement of the specimen, it is necessary to set this period T to any time which however will be relatively reasonable, of the order of a half hour or an hour. It will therefore suffice to obtain this rapid operation to chose a thickness E of the specimen which will be small so as to impose little constraint on the measurement.

Under these conditions, the central separation plate 1 being at all times at a uniform temperature, it is possible to know the value of the flux exchanged between the specimens 2a, 2b and the separation plate 1. Thus, under the conditions given above, an overall heat transfer H during a time interval t gives rise to a temperature rise $\Delta T$:

$$H = m \, Cp \, \Delta T.$$

If S is the lateral surface of the plate, $\gamma$, $Cp$ the characteristic values of its material, the mean heat flux can be directly calculated between t and $t = \Delta t$:

$$\Phi m = \Delta H / 2 S \times \Delta t = \tfrac{1}{2} \gamma Cp E p \Delta t / \Delta t$$

The measurement of the volumetric mass $\gamma$ generally poses no problem and can be effected with high precision. As to the tolerance for E, p it is small by construction. Knowledge of the flux permits then a precise identification of the conductivities and the contact resistance values. An example of embodiment of a conductivity meter and of the determination of the conductivity of a specimen of a material to be studied will be given hereafter.

Figure 2:
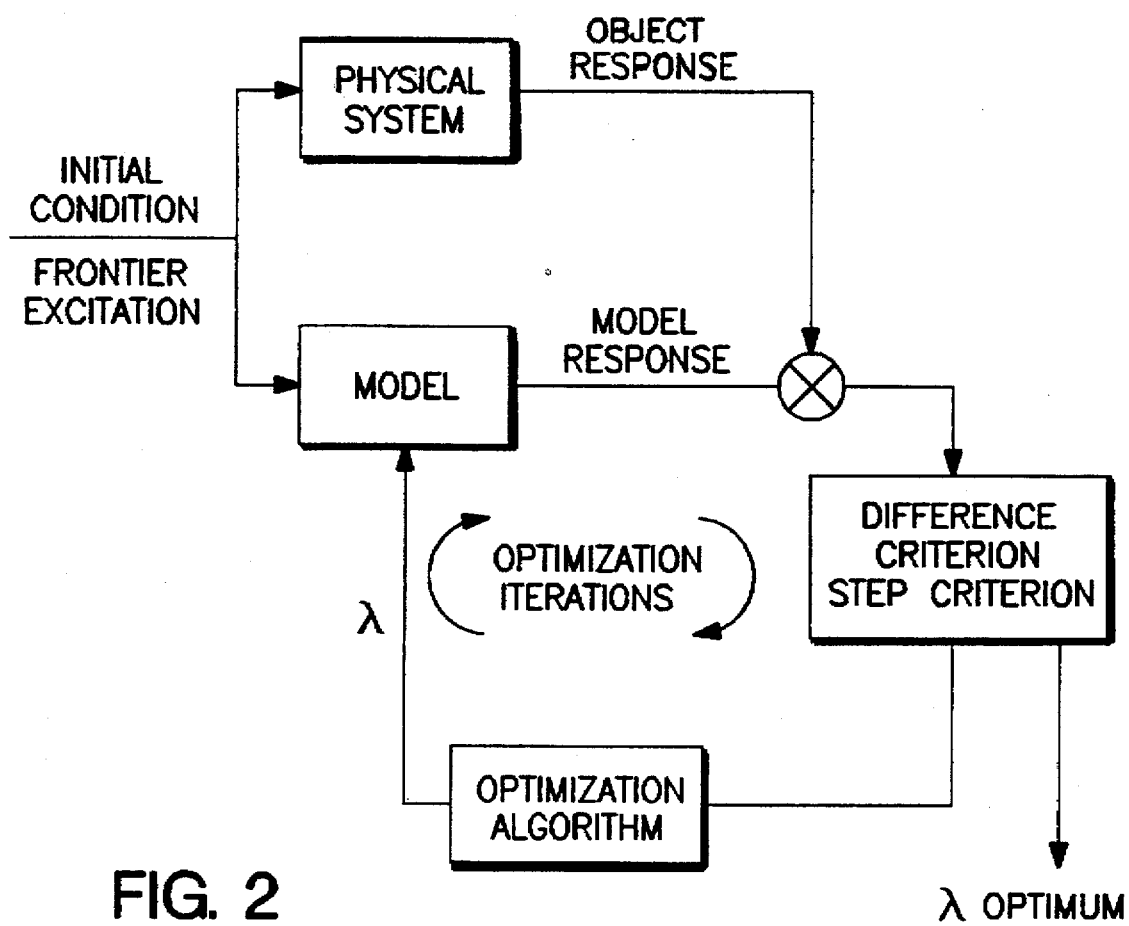
FIG. 2 is an operational scheme of the process of identification of conductivity.

The data obtained are constituted particularly by the temperature curves T1 (t), T2 (t), T3 (t). To identify the conductivity of the specimen of the material to be studied, there is used an identification method whose functional scheme is represented in FIG. 2. In this identification method, there is used a physical system constituted by the conductivity meter itself as described above. This physical system is subjected to a known excitation permitting obtaining the temperature change with time, this change is called the object response (T1 (t), T2 (t), T3 (t)). In parallel to this physical system, there is used a model constituted by a thermal system which is described by a series of non-linear partial differential equations over the time range [0,tF] and within a space [0, L], L corresponding to the distance separating a heat exchange plate from the central separation plate. This system permits obtaining a certain number of solutions calculated from measurement points obtained from the physical system. These solutions are called design response. This response depends on P unknown parameters of the equation. These parameters form the vector $\beta e$ which must be identified. A is called "admissible series of parameters" and in practice, the series is defined by their minimum and maximum values. In the problem under consideration, $\beta$ is defined by (1) $\beta = (\lambda 1, \ldots, \lambda i, \ldots, \lambda_{NI}, R1_1, \ldots, R1_j, \ldots, R1_{NJ}, \ldots, R2_1, \ldots, R2_1, \ldots, R2_{NL})$ (1a) $p = NI + NJ + NL$ in which $\lambda i$ is the conductivity at temperatures $\Phi i$ and $R1_j$ and $R2_l$, the contact thermal resistances for the instant j and l respectively. The identification consists in the determination of $\beta^*$, a value of $\beta$, such that the design response will be as close as possible, the criterion remaining to be defined, to the object response. To find $\beta^*$, a descent method is utilized. This is an iterative method which consists in calculating a series $\beta 0$, $\beta 1$, $\beta I$ (in A) which satisfies $J(\beta o > J(\beta 1) > \ldots > J\beta i$.

The specimen temperature $\theta$ (x, t) in the spatial domain (0, L) limited by two interfaces and the temperature $\theta_1$ of the first layer at the interface x=0, are a solution of $$C(\theta) \frac{\partial \theta}{\partial t}(x,t) - \frac{\partial}{\partial x}\left[ \lambda(\theta) \frac{\partial \theta}{\partial x}(x,t) \right] = 0 \quad 0 < x < L \quad (3)$$

$$\theta_j(t) = \theta(0,t) - R1(t)\phi_1(t) \quad x = 0 \quad (3a)$$

$$-\lambda(\theta) \frac{\partial \theta}{\partial x}(0,t) = \phi_j(t) \quad x = 0 \quad (3b)$$

$$R2(t)\left[ \lambda(\theta)\frac{\partial \theta}{\partial x}(L,T) \right] + \theta(L,t) = T_2(t) \quad x = L \quad (3c)$$

The data are:

measurements: $\Phi_1(t)$, $T_1(t)$ and $T_2(t)$, for $0 < t < t_f$
parameters: $C(\theta) = (\theta) \, Cp \, (\theta)$, and L
initial conditions: $\theta_1(0)$ and $\theta(x, 0)$ for $0 < x < L$ The general expression of the criterion J is:

$$J(\beta) = \sum_{k=1}^{n} (\theta_1(t_k, \beta) - T_1(t_k))^2 w_k + \sum_{i=1}^{p} (\mu_i - \beta_i)^2 u_i \quad (4)$$

in which:

$w_k$—is the instantaneous positive weight coefficient k, which can include several data according to the experimental errors, $u_i$—is a non-negative weight coefficient for i-th component of $\beta$, $\mu_i$—is an initial estimate of $\beta$.

This spacing criterion J ($\beta$) permits minimizing the space between the measured temperatures in the central plate and the calculated temperatures for the same point and at the same time by the design. This adjustment is made by an inverse method based on the method principle of Gauss-Newton (see J. V. Beck "Parameter estimation in Engineering and Science", Wiley 1977).

This minimization has an iterative character, which is to say that the characteristics are successively adjusted until the spacing criterion J ($\beta$) is equal to a value which corresponds to an end condition of the calculation.

Thus, by way of example, let there be supposed a device according to the invention of the type below.

Figure 4:
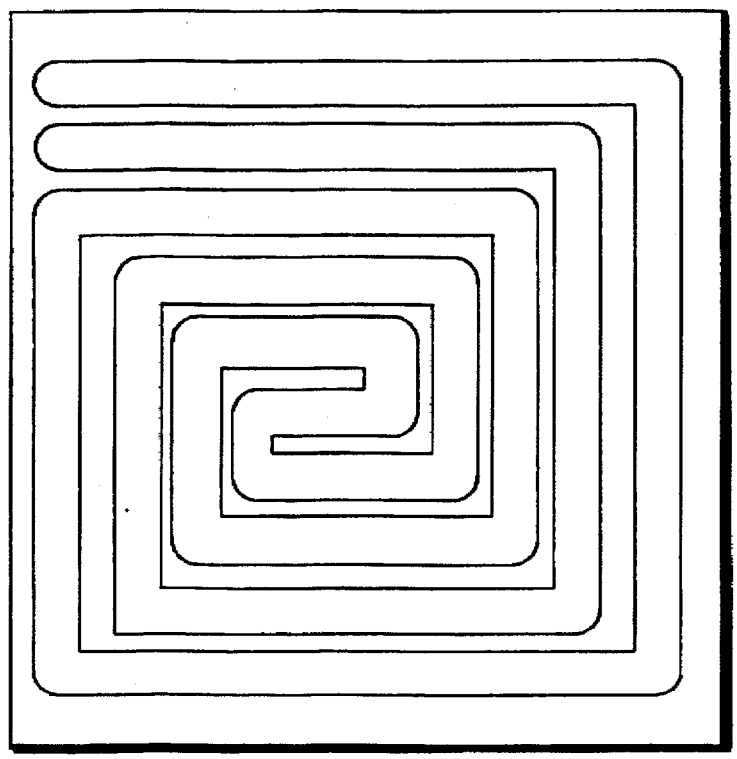
FIG. 4 is a plan view of a plate exchanger adapted to be used in the conductivity meter.

The lateral exchangers 3a and 3b are conventional exchangers known per se of the calporter fluid circulation type as shown in FIG. 4. This fluid is from a temperature controlled bath (4a or 4b). The flow rate of the fluid inside the exchanger is generally of the order of 20 l/mn. These exchangers are generally of aluminum.

The central plate 1 is also of aluminum and has for example the following dimensions: 140×140×4 mm.

As to the specimens, they are in the considered example in the form of plates of plexiglass (140×140×12 mm).

From this: $(Ep/E)^2 0.1 \, \alpha_p/\alpha_E \times 1/\Delta \, T$ corresponds to $(\tfrac{4}{12})^2 < 0.1 \, 8.42 \times 10^{-5} .1$ The insulation is itself constituted by polystyrene.

Figure 3:
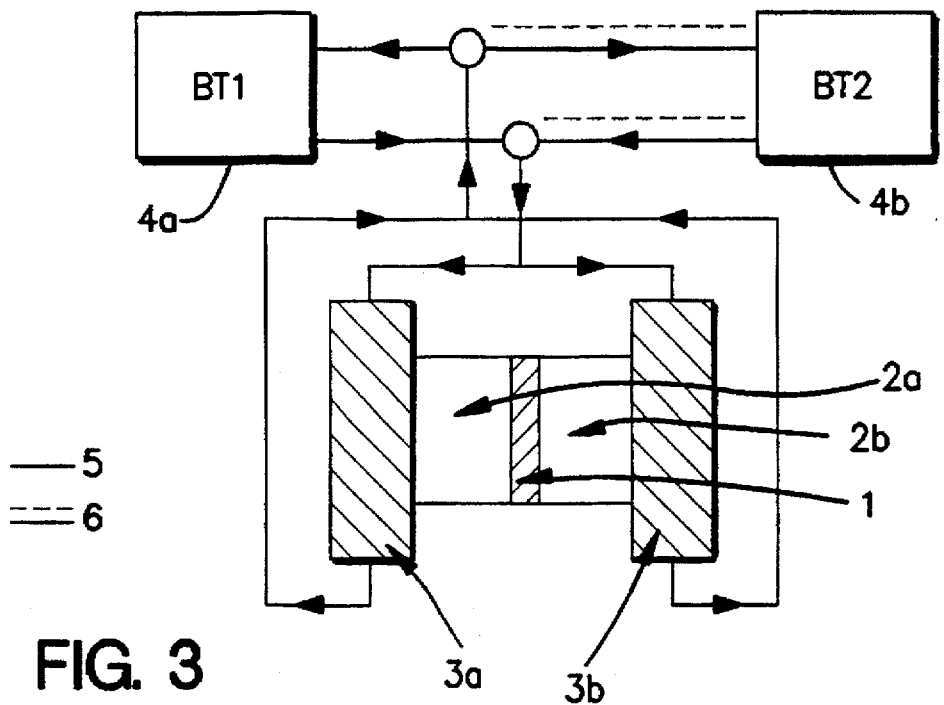
FIG. 3 is a simplified schematic view of the conductivity meter and of the circulation of fluids in the exchangers.

The heat exchangers are supplied by means of two fluid circuits 5 and 6 shown in FIG. 3. In the first instance, at the beginning of the operation, only the circuit 5 is used. This circuit operates for several minutes and permits obtaining an initial temperature T0 of the central plate 1 corresponding to one of the end values of the temperature range in question. When this temperature is constant, and therefore when the circuit is in thermal equilibrium, the measurement can be conducted. At the time t=0 of measurement, the circuits 5 and 6 are reversed and it is then the circuit 6 which will ensure heating or cooling of the specimens. Two temperature controlled baths labelled BT1 and BT2 are used to decrease the duration of the operation.

Figure 5A:
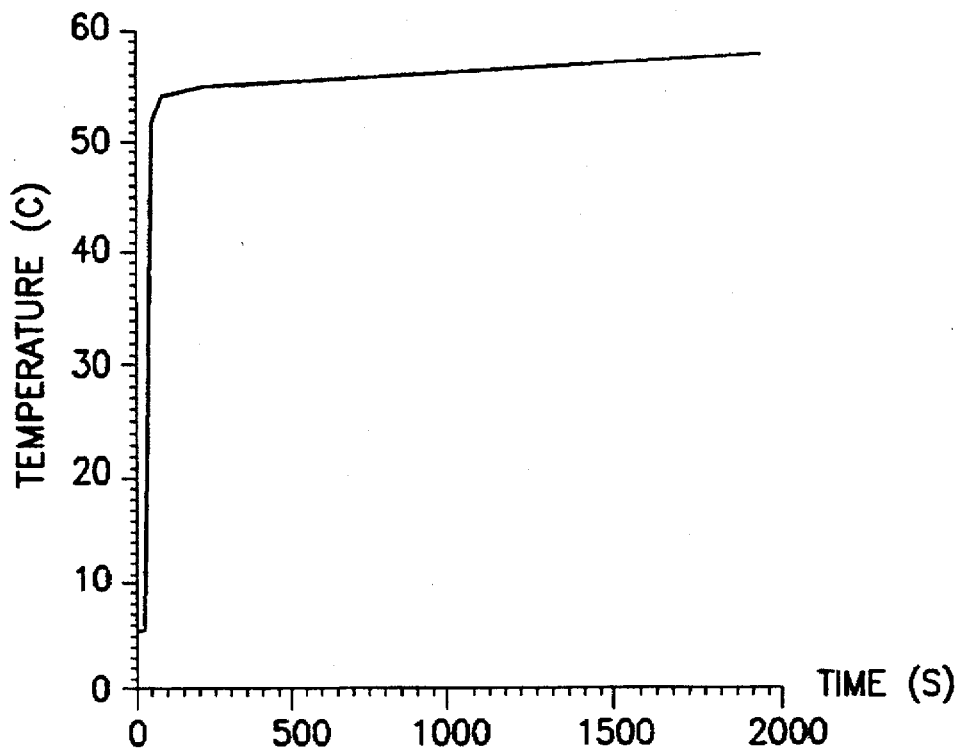
FIG. 5a is the curve of temperature measured by the thermocouple 1 as a function of time.
Figure 5B:
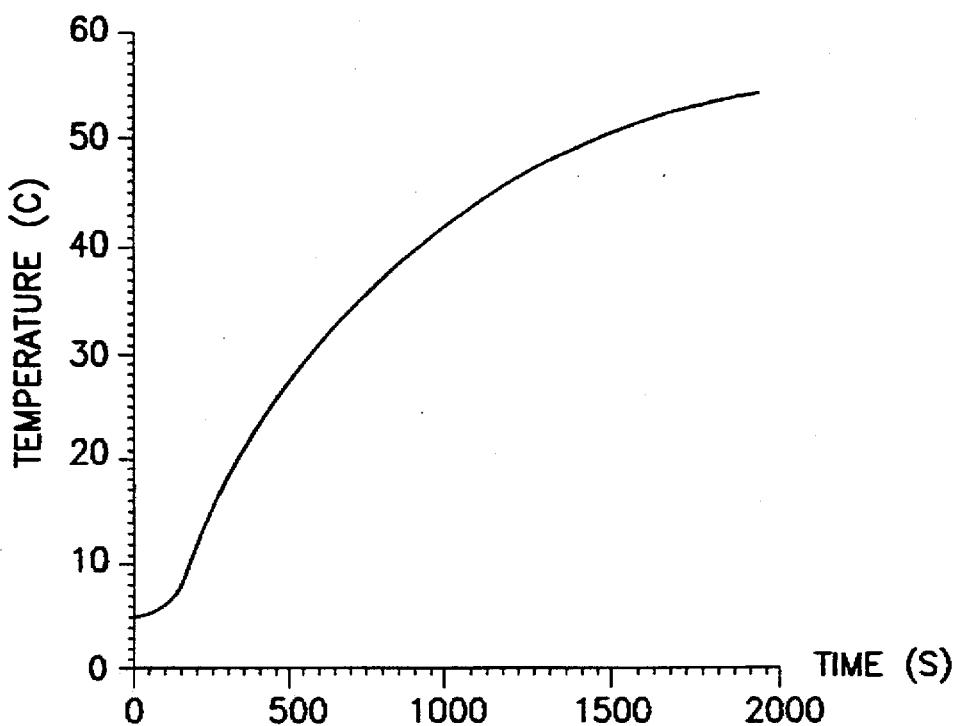
FIG. 5b represents the temperature measured by the thermocouple 2 as a function of time.

There are thus obtained curves T=f (t) shown in FIGS. 5a and 5b. Of course the curve that can be obtained from thermocouple T3 has not been shown because it will, in the absence of any technical mishap, be identical to that of FIG. 5a.

This data acquisition is effected by means of a computer of the PC type and of a voltmeter for example (Keithley 199 scanner made by Keithley).

Thanks to the data obtained by means of the thermocouple T2 of the central plate 1, the heat flow can be calculated varying the temperature of the central plate and passing through one surface of the specimen using the following formula:

$$\Phi p = \frac{1}{2} Cp Ep \Delta T / \Delta t$$

Figure 6:
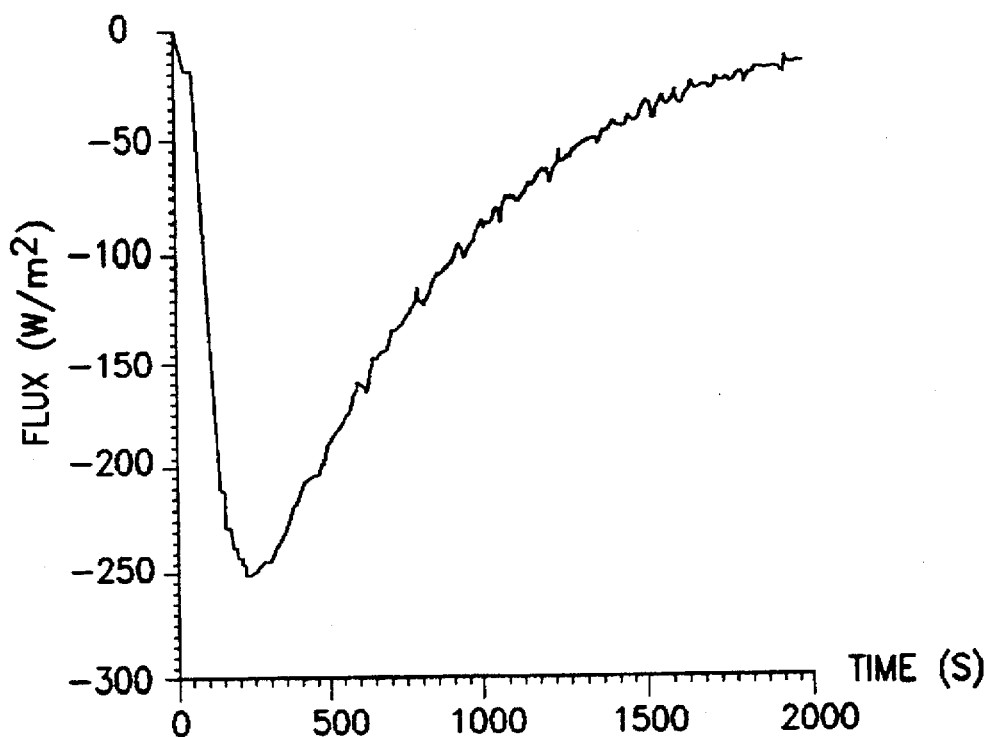
FIG. 6 shows the curve of heat flow calculated as a function of time.

There is then obtained a curve $\Phi p = f(t)$ according to that shown in FIG. 6.

Then in a third step, the identified parameters are begun: in the example under consideration, the identified parameters are:

the thermal conductivity of the plexiglass (specimen) $\lambda$ and the contact resistances aluminum/plexiglass: R1, R2 and have a value $$\lambda = 0.189 \; Wm^{-1} \; k^{-1}$$

$$R1 = R2 = 1.10^{-5} \; km^2 \; w^{-1}$$

The following data are introduced:
volumetric specific heat of specimen: $Cp = 10527.10^6 \; Jk^{-1} \; m^{-2}$
thickness of the specimen.

It will be noted that a large error can occur in the value of Cp without affecting significantly the value of the identified conductivity of the specimen.

There is applied to these data the identification algorithm under limited conditions of flow, L and the corresponding respective temperature in FIGS. 6 and 5a. The temperature of the plate is then calculated. The heat equation is then solved so as to obtain an assembly of computational results, then the criterion J described above is calculated.

If the criterion J satisfies the stopped condition, the value of the conductivity is optimum unless the parameters are modified that have been optimized by means of the Gauss Newton method.

Figure 7:
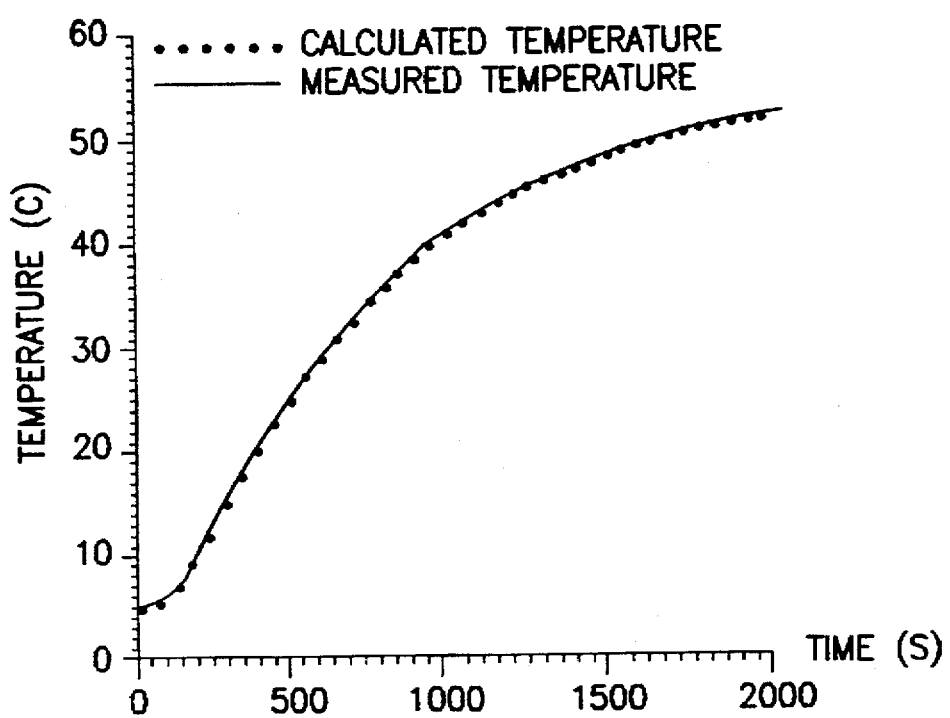
FIG. 7 shows the curves of temperatures of the central plate measured and calculated after convergence of the algorithm as a function of time.

There is shown in FIG. 7 the comparison between the calculated plate temperature and this measured temperature, when the algorithm has converged.

It will be seen that the values identified for the resistances are very low, of the order of $1.10^{-5}$ because the contact was practically perfect. The value identified for conductivity is constant and very close to the reference values ($\lambda = 0.19 \; Wm^{-1} \; k^{-1}$).

The measurement device and the associated identification method can be used by manufacturers of software, producers of material for testing the characteristics of their products, material processors particularly in the field of quality control procedures.

We claim:
1. Measuring device for measuring in a transitory manner at least one of the conductivity and the heat capacity of a material, which comprises:

two heat exchangers with flat walls disposed on opposite sides of a central separation plate having parallel walls sufficiently conductive to be considered isothermal without any fluid passing through said central plate, said flat walls delimiting with said plate two substantially identical chambers;

heating and cooling means for said heat exchangers;

two specimens of the material to be studied, of similar thickness, disposed in said chambers respectively between an external surface of the flat wall of the respective heat exchanger and one surface of the central separation plate so as to be traversed by a heat flow;

means for positioning and holding the heat exchangers substantially parallel to the central plate so as to ensure homogeneous pressure contact between the walls of the heat exchangers, the external surfaces of the specimens, and the surfaces of the central separation plate;

insulation means closing remaining free edges of said chambers for providing unidirectional heat flow; and at least two temperature sensors of which one T2, constituted by a thermocouple is integrated into the central separation plate, and of which the other T1, constituted also by a thermocouple is integrated into the external surface of the flat wall of one of the heat exchangers.

2. Measuring device according to claim 1, further comprising a third temperature sensor constituted by a thermocouple T3 integrated on the external surface of the flat wall of the other heat exchanger.

3. Measuring device according to claim 2, wherein recordation of temperature curves of temperatures sensed by the thermocouples is effected over a period for a temperature variation only when thermal equilibrium of the device is reached.

4. Measuring device according to claim 1, wherein the respective thickness Ep and E of the central separation plate and one of the specimens to be studied are selected such that:

$$(Ep/E^2) < 0.1 \; \alpha_P/\alpha_E \times 1/\Delta\theta$$

and $$Ep/E \leq 0.5,$$

$\alpha_P$ and $\alpha_E$ being the respective diffusivities of the plate and of the specimen, $\Delta\theta$ being an externally imposed range of variation of temperature.

5. Measuring device according to claim 1, wherein the insulation means has a thermal conductivity less than 0.1 w/m/k and a heat capacity lower than $2\times10^5$ J/kg/K.

6. Measuring device according to claim 1, wherein the thickness E of one of the specimens to be studied satisfies the following relationship:

$$E^2 \leq \lambda T\pi^2/\gamma Cp$$

$\lambda$, $\gamma$, Cp being respectively the conductivity, the volumetric mass, and the volumetric specific heat at the temperature of the specimen to be studied, and T is the maximum delay necessary to reach thermal equilibrium.

7. Measuring device according to claim 1, wherein the means for positioning and holding the heat exchangers is constituted by movable plates of a press whose facing surfaces are secured to said heat exchangers.

* * * * *